United States Patent
Jaworski et al.

(10) Patent No.: US 8,928,883 B1
(45) Date of Patent: Jan. 6, 2015

(54) OPTICAL DEVICE FOR DETECTION OF AN AGENT

(75) Inventors: Frank B. Jaworski, Goleta, CA (US); Justin Gordon Adams Wehner, Goleta, CA (US); Adam M. Kennedy, Santa Barbara, CA (US); Darin S. Williams, Tucson, AZ (US); Anuradha Murthy Agarwal, Weston, MA (US); Juejun Hu, Newark, DE (US)

(73) Assignee: Raytheon Company, Waltham, MA (US)

( * ) Notice: Subject to any disclaimer, the term of this patent is extended or adjusted under 35 U.S.C. 154(b) by 804 days.

(21) Appl. No.: 12/948,485

(22) Filed: Nov. 17, 2010

Related U.S. Application Data

(63) Continuation-in-part of application No. 12/503,264, filed on Jul. 15, 2009, now Pat. No. 8,394,329.

(60) Provisional application No. 61/223,546, filed on Jul. 7, 2009, provisional application No. 61/262,053, filed on Nov. 17, 2009.

(51) Int. Cl.
*G01N 21/00* (2006.01)

(52) U.S. Cl.
USPC .............. 356/433; 250/227.17; 250/227.19; 356/432; 385/12; 385/30; 385/39

(58) Field of Classification Search
CPC ............. G01N 2021/7776; G01N 2021/7783; G01N 2021/7789
USPC ............... 356/433, 432; 250/227.14, 227.19; 385/12, 15, 30
See application file for complete search history.

(56) References Cited

U.S. PATENT DOCUMENTS

| | | | |
|---|---|---|---|
| 7,027,467 B2 | 4/2006 | Baev et al. | |
| 7,389,025 B2 * | 6/2008 | Smith et al. | 385/39 |
| 7,391,517 B2 | 6/2008 | Trebbia et al. | |
| 7,432,753 B2 | 10/2008 | Onodera | |
| 7,595,890 B2 | 9/2009 | Fan et al. | |
| 7,667,200 B1 | 2/2010 | Watts et al. | |
| 2002/0097401 A1 | 7/2002 | Maleki et al. | |

(Continued)

OTHER PUBLICATIONS

Hu et al., "Si-CMOS-compatible lift-off fabrication of low-loss planar chalcogenide waveguides," *Optics Express*, vol. 15, No. 19, Sep. 17, 2007.

(Continued)

*Primary Examiner* — Gregory J Toatley
*Assistant Examiner* — Iyabo S Alli
(74) *Attorney, Agent, or Firm* — Lando & Anastasi, LLP

(57) ABSTRACT

In certain embodiments, a system for detecting an agent includes a resonator device configured to receive an agent. The resonator device is also configured to transmit light received from a light source, the transmitted light having an altered peak wavelength due to the presence of the received agent. The system further includes a filter device configured to filter the transmitted light having the altered peak wavelength such that the transmitted light having the altered peak wavelength does not reach one or more detectors of a detector array configured to receive transmitted light not filtered by the filter device. The system further includes a processing system operable to determine that the one or more detectors of the detector array are not generating a signal, the absence of the signal being generated by the one or more detectors of the detector array indicating the presence of the agent.

21 Claims, 4 Drawing Sheets

(56) References Cited

U.S. PATENT DOCUMENTS

| | | |
|---|---|---|
| 2005/0035278 A1* | 2/2005 | Margalit et al. .......... 250/227.14 |
| 2005/0110992 A1* | 5/2005 | Scherer et al. ................ 356/318 |
| 2005/0207943 A1 | 9/2005 | Puzey |
| 2006/0062508 A1 | 3/2006 | Guo et al. |
| 2006/0072875 A1 | 4/2006 | Bhagavatula et al. |
| 2006/0227331 A1 | 10/2006 | Vollmer et al. |
| 2007/0211985 A1* | 9/2007 | Duer .............................. 385/12 |
| 2008/0204758 A1 | 8/2008 | Yates et al. |
| 2008/0265147 A1* | 10/2008 | Fan et al. ................. 250/227.24 |
| 2009/0237666 A1 | 9/2009 | Vollmer et al. |
| 2009/0310140 A1 | 12/2009 | Smith et al. |
| 2010/0243448 A1 | 9/2010 | Maurer et al. |
| 2011/0080579 A1 | 4/2011 | Pipino |
| 2011/0256577 A1 | 10/2011 | Himmelhaus et al. |
| 2011/0295511 A1 | 12/2011 | Sanders et al. |
| 2012/0154810 A1 | 6/2012 | Jaworski et al. |

OTHER PUBLICATIONS

Hu et al., "Demonstration of chalcogenide glass racetrack microresonators," *Optics Letters*, vol. 33, No. 8, pp. 761-763, Apr. 15, 2008.

Jaworski et al, U.S. Appl. No. 12/503,264 "Optical Device for Detection of Agent" filed Jul. 15, 2009.

Jaworski et al, U.S. Appl. No. 12/948,453 "Optical Device for Detection of Agent" filed Nov. 27, 2010.

Frank B. Jaworski, U.S. Appl. No. 13/173,221 "Optical Device for Detection of Agent" filed Jun. 30, 2011.

\* cited by examiner

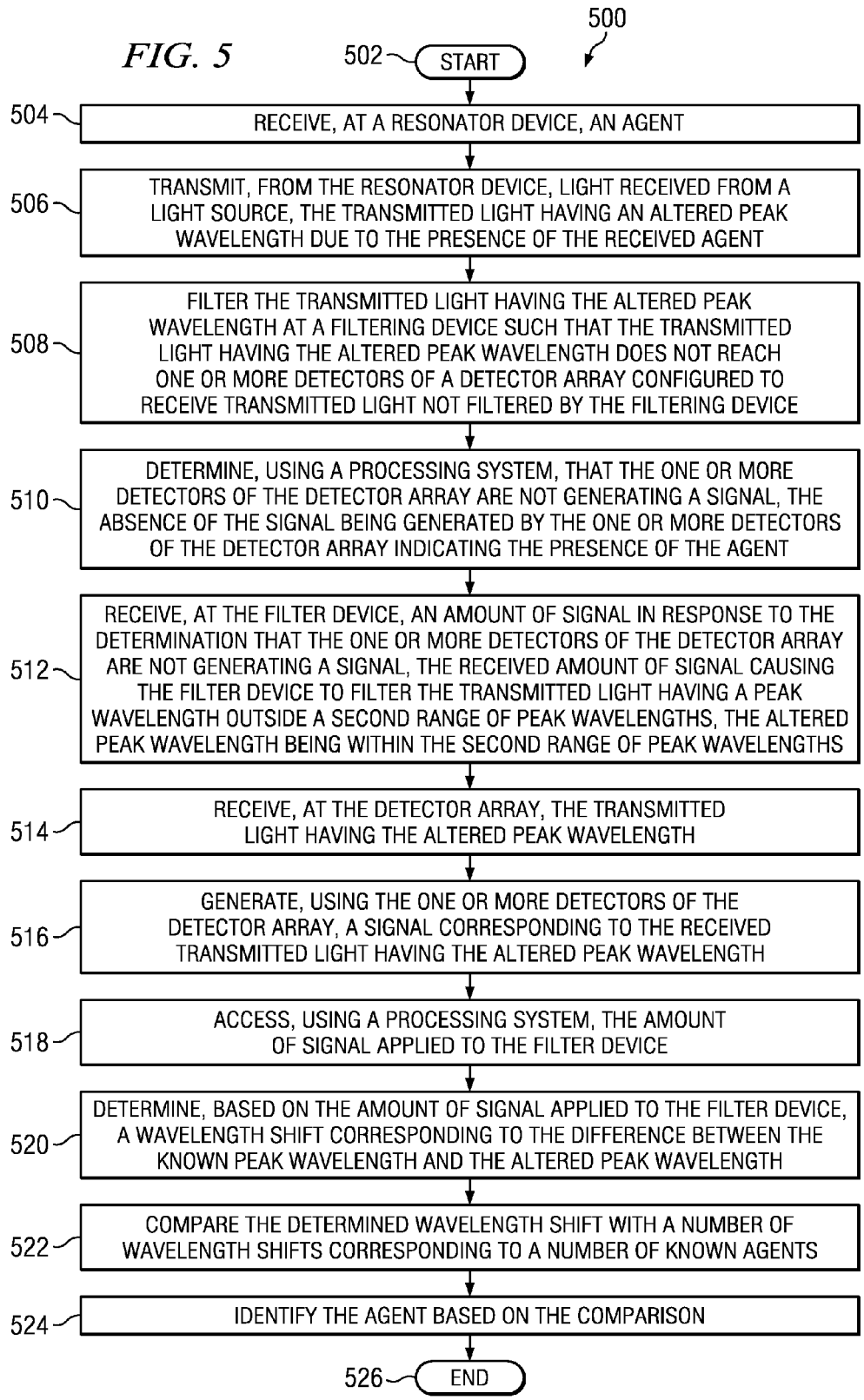

US 8,928,883 B1

OPTICAL DEVICE FOR DETECTION OF AN AGENT

RELATED APPLICATIONS

This application is a continuation-in-part of U.S. application Ser. No. 12/503,264 filed Jul. 15, 2009 now U.S. Pat. No. 8,394,329, which is a non-provisional of U.S. Application Ser. No. 61/223,546 filed Jul. 7, 2009, the entire contents of which are hereby incorporated by reference. Additionally, this application claims the benefit under 35 U.S.C. §119(4) of the priority of U.S. Provisional Application No. 61/262,053, filed Nov. 17, 2009, entitled "Optical Device for Detection of an Agent," the entire contents of which is hereby incorporated by reference.

TECHNICAL FIELD

This invention relates generally to agent detection and more particularly to an optical device for detection of an agent.

BACKGROUND

Detector arrays, such as focal plane arrays (FPAs), generally comprise a number of photo-detectors each operable to generate a signal corresponding to one or more characteristics of light incident on the surface of the detector array. Imaging devices commonly use detector arrays to generate digital images. In such applications, the photo-detectors of the detector array each generate a signal corresponding to light generated and/or reflected by an object. The generated signals may be collected and combined such that a digital image of the object that generated and/or reflected the light may be generated.

SUMMARY

According to embodiments of the present invention, disadvantages and problems associated with previous systems for detection of an agent may be reduced or eliminated.

In certain embodiments, a system for detecting an agent includes a resonator device configured to receive an agent. The resonator device is also configured to transmit light received from a light source, the transmitted light having an altered peak wavelength due to the presence of the received agent. The system further includes a filter device configured to filter the transmitted light having the altered peak wavelength such that the transmitted light having the altered peak wavelength does not reach one or more detectors of a detector array configured to receive transmitted light not filtered by the filter device. The system further includes a processing system operable to determine that the one or more detectors of the detector array are not generating a signal, the absence of the signal being generated by the one or more detectors of the detector array indicating the presence of the agent.

Particular embodiments of the present invention may provide one or more technical advantages. For example, embodiments of the present invention may use a detector array (such as an FPA) to detect changes in characteristics of light passing through an agent. As a result, embodiments of the present invention may be incorporated into a portable device, which may reduce size, weight, cost, and power requirements as compared to certain conventional systems for detecting an agent. Moreover, because embodiments of the present invention may use detector arrays which may be common in certain imaging devices, the present invention may be integrated with or form part of an imaging device.

Certain embodiments of the present invention may include some, all, or none of the above advantages. One or more other technical advantages may be readily apparent to those skilled in the art from the figures, descriptions, and claims included herein.

BRIEF DESCRIPTION OF THE DRAWINGS

To provide a more complete understanding of the present invention and the features and advantages thereof, reference is made to the following description taken in conjunction with the accompanying drawings, in which:

FIG. 5 illustrate an example alternative method for detecting an agent, according to certain embodiments of the present invention.

DESCRIPTION OF EXAMPLE EMBODIMENTS

Figure 1:
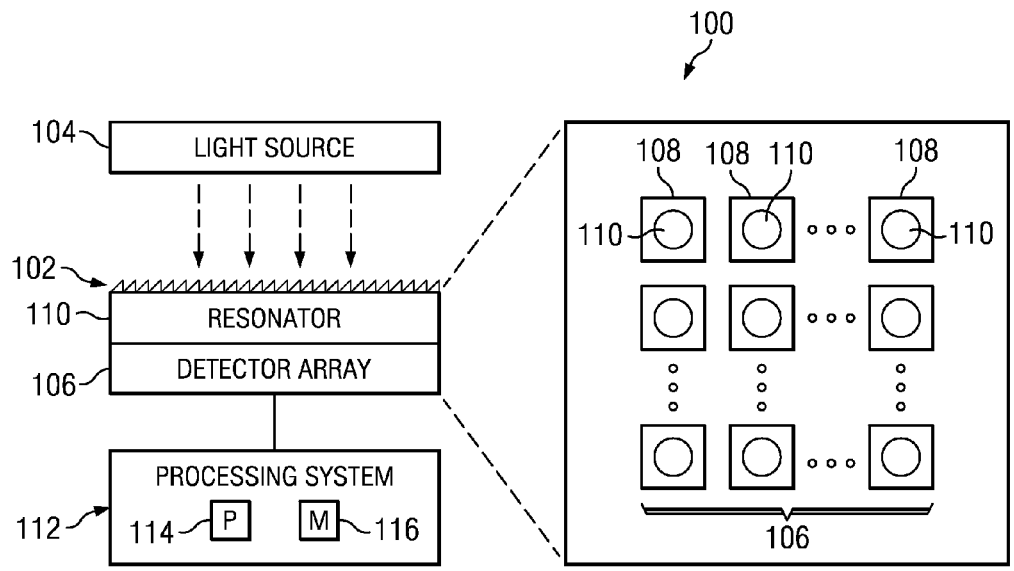
FIG. 1 illustrates an example system for detecting an agent, according to certain embodiments of the present invention.

FIG. 1 illustrates an example system 100 for detecting an agent 102, according to certain embodiments of the present invention. System 100 may include one or more light sources 104, a detector array 106 comprising one or more detectors 108, and one or more resonators 110 configured to receive (e.g., absorb) an agent 102. In certain embodiments, the one or more detectors 108 of detector array 106 are configured to communicate with a processing system 112 operable to identify an agent 102 (or identify a family of agents to which agent 102 belongs) based on one or more characteristics of light sensed by detectors 108 of detector array 106. Although this particular implementation of system 100 is illustrated and primarily described, the present invention contemplates any suitable implementation of system 100, according to particular needs.

In general, system 100 is operable to detect the presence of an agent 102. Agent 102 may refer to one or more atoms or molecules of any chemical, biological, and/or physical matter the presence of which may be detected by system 100. As just example, agent 102 may include a hazardous substance such as a chemical or biological agent. Furthermore, system 100 may be in incorporated into a handheld device to be carried by military personnel, the handheld device operable to detect chemical or biological agent 102 (e.g., in the air, in water, or in any other suitable medium) such that the military personnel may be alerted to the presence of the chemical or biological agent 102. Although a particular application of system 100 (e.g., incorporated into a handheld device to be carried by military personnel) is described above, the present invention contemplates any suitable application of system 100, according to particular needs.

System 100 may detect an agent 102 based on signal generated by detectors 108 of detector array 106. More particularly, detectors 108 of detector array 106 may be operable to generate a signal corresponding to one or more characteristics of light (e.g., intensity and/or peak wavelength) transmitted by a resonator 110. Because a resonator 110 may have known optical properties, light transmitted by the resonator 110 may have known characteristics. Thus, the signal generated by detectors 108 of detector array 106 may also be known (i.e., a signal generated by transmitted light received by detectors 108 having known characteristics corresponding to the known optical properties of the resonator 110).

If agent 102 is received by (e.g., absorbed on a surface of) resonator 110, the characteristics of the light transmitted by resonator 110 may be altered by the agent 102. For example, agent 102 may absorb an amount of the transmitted light (i.e., decrease the intensity of the transmitted light), or agent 102 may alter the peak wavelength of the transmitted light. As a result, the signal generated by detectors 108 of detector array 106 may differ from the known signal. Thus, when the signal generated by a particular detector 108 of detector array 106 differs from the known signal associated with that detector 108, it may be determined that an agent 102 is present on the surface of the resonator 110 corresponding to the detector 108.

Because system 100 uses a detector array 106 (such as an FPA, as described below), system 100 may be incorporated into a portable device. As a result, system 100 may provide for the detection of agents 102 in a system having reduced size, weight, cost, and power requirements as compared to conventional systems for detecting an agent 102. Moreover, because detector array 106 of system 100 may be common in certain imaging devices, system 100 may be integrated with or form part of an imaging device.

Light sources 104 of system 100 may include any suitable devices operable to emit an amount of light such that the emitted light may be received by one or more resonators 110. For simplicity, the one or more light sources 104 will be referred to primarily in the singular throughout the remainder of this description. In other words, it will be assumed that a single light source 104 provides light received by each resonator 110, as described in further detail below; however, the present invention contemplates system 100 including any suitable number of lights sources 104.

Light source 104 may be a broadband light source operable to emit an amount of light having a range of wavelengths. In certain embodiments, light source 104 is an on-chip light source. In other words, light source 104 may be coupled to detector 106, which is in turn coupled to one or more other components of system 100 (e.g., detector array 106 and/or processing system 112) such that the combination of components forms a single semiconductor device (e.g., a chip). For example, light source 104 may be an on-chip quantum dot light emitting diode (LED), an on-chip laser, or any other suitable on-chip light source, according to particular needs.

Detector array 106 of system 100 may be a focal plane array (FPA), active pixel sensor (APS), or any other suitable light sensing device operable to generate a signal corresponding to one or more characteristics of light incident upon detector array 106. Detector array 106 may include any suitable number of detectors 108, and each detector 108 may be operable to generate a signal (e.g., accumulate charge or produce a current and/or voltage) in response to light incident upon the detector 108. For example, detectors 108 may include a position sensitive detector (PSD), photodiode, and/or any other suitable device for accumulating a charge and/or producing a current and/or voltage in response to light incident upon the detector 108.

In certain embodiments, detector array 106 may be a component of a digital camera, video camera, or any other photographic and/or image capturing device. In such applications, the signal generated by detectors 108 (e.g., the charge accumulated or the current and/or voltage produced) may be further processed (e.g., by processing system 112, described below) to create an image representative of an object emitting and/or reflecting the incident light. In other words, the signal generated by each detector 108 may correspond to a pixel in a captured electronic image.

The one or more resonators 110 of system 100 may each include any suitable device constructed from any suitable material that has known optical properties. In other words, each resonator 110 may be any suitable device that is configured to receive light from light source 104 and transmit the received light such that the transmitted light has known characteristics (e.g., intensity and/or peak wavelength). For example, resonators 110 may be devices constructed of chalcogenide glass and configured to receive broadband light from light source 104 and transmit light having a particular peak wavelength (or range of peak wavelengths). In other words, resonators 110 may filter the broadband light received from light source 104 such that light having a particular wavelength (or range of peak wavelengths) is transmitted from resonators 110.

In certain embodiments, resonators 110 comprise waveguides configured in a closed loop known as an optical ring such that light received from lights source 104 of the appropriate wavelengths are coupled to the loop, the light increasing in intensity over multiple round-trips due to constructive interference. Other wavelengths of light received from light source 104 may decrease in intensity due to destructive interference. In certain other embodiments, resonators 110 comprise an arrangement of mirrors known as an optical cavity, the optical cavity being configured to form a standing wave for one or more wavelengths.

Each resonator 110 may correspond to (i.e., be coupled to or otherwise configured to transmit light to) one or more detectors 108 of detector array 106. Although each resonator 110 is depicted as corresponding to a single detector 108 of detector array, the present invention contemplates each resonator 110 corresponding to any suitable number of detectors 108, according to particular needs. For purposes of simplicity, each resonator 110 will be described throughout the remainder of this description as corresponding to a single detector 108.

Resonators 110 may be configured to receive agent 102, and agent 102 may alter the known characteristics of light transmitted by the resonators 110 (as described in further detail below). Resonators 110 may receive agent 102 in any suitable manner. For example, resonators 110 may be configured to receive an agent 102 by absorbing the agent 102 from a liquid including the agent 102, which may be deposited on a surface of resonators 110 (e.g., by a user of system 100). Alternatively, resonators 110 may be configured to receive an agent 102 (e.g., an airborne agent) by absorbing the agent from air containing the agent 102. Furthermore, one or more resonators 110 may be functionalized (e.g., by coating a surface with artificial antibodies using a polymer technique) such that the one or more resonators attract only certain agents 102 or families of agents 102.

If an agent 102 is received (e.g., absorbed) by one or more resonators 110, the agent 102 may alter the characteristics of light transmitted by the one or more resonators 110. For example, certain agents 102 may absorb a particular amount of received light (i.e., decrease the intensity of light as compared to a known intensity based on the optical properties of the resonator 110), other agents 102 may change the index of refraction of received light (i.e., change the peak wavelength of light relative to a known intensity based on the optical properties of the resonator 110), and still other agents 102 may both absorb a particular amount of light and change the index of refraction of light.

As described above, resonators 110 have known optical properties. Due to these known optical properties, resonators 110 transmit light having known characteristics such that the signals to be generated by the detectors 108 corresponding to the resonators 110 (in the absence of an agent 102) may be known. Because an agent 102 may alter one or more characteristics of light transmitted by resonators 110, in the presence of an agent 102, the signals generated by the corresponding detectors 108 may differ from the known signal (i.e., detectors 108 may generate altered signals rather than known signals). Thus, by determining whether a signal generated by a detector 108 differs from the known signal associated with the detector 108, whether an agent 102 is present may also be determined (as described in further detail below). Additionally, because different agents 102 may alter one or more characteristics of light transmitted by resonators 110 in different ways (which may affect the degree of difference between the altered signal and the known signal), the way in which the characteristics of light transmitted by resonators 110 is altered may be used to identify agent 102 or the family of agent 102 (as described in further detail below).

Processing system 112 of system 100 may include any suitable combination of software, firmware, and hardware may comprise a personal computer, workstation, network computer, kiosk, wireless data port, personal data assistant (PDA), one or more processors within these or other devices, or any other suitable processing device. Processing system 112 may include one or more processing modules 114, which may include one or more microprocessors, controllers, or other suitable computing devices or resources that may work either alone or with other components of system 100 to provide a portion or all of the functionality of system 100 described herein. Processing system 112 may also include one or more memory modules 116, which may take the form of volatile or non-volatile memory including, without limitation, magnetic media, optical media, random access memory (RAM), read-only memory (ROM), removable media, or any other suitable memory component.

Additionally or alternatively, processing system 112 may comprise a read-out integrated circuit (ROIC) hybridized to detector array 106, the ROIC having any suitable processing components and memory components (e.g., processing module 114 and memory module 116), according to particular needs. Although processing system 112 is primarily described as being either of the above described systems, the present invention contemplates processing system 112 being any suitable system operable to perform the functionality described below.

Processing system 112 may be operable to access signals generated by the one or more detectors 108 of detector array 106, and to determine if an agent 102 is present (i.e., absorbed on the surface of one or more resonators 110). In response to an input (e.g., a user request), at any suitable time interval without user input (e.g., periodically determining if an agent has been received, for example, absorbed from air), or in response to any other suitable input, processing system 112 may access signals generated by one or more detectors 108 of detector array 106 and determine if an agent 102 is present. Additionally, if processing system 112 determines that an agent 102 is present, processing system 112 may be further operable to identify the agent 102 (or a family of the agent 102).

In certain embodiments, processing system 112 determines if an agent 102 is present by analyzing the accessed signals to determine if one or more of the signals indicate a change in intensity of light received by the detectors 108 generating the one or more signals. For example, processing system 112 may access the signal generated by a particular detector 108 and compare the generated signal with a known signal associated with the particular detector 108. The known signal associated with the particular detector 108 may be stored in memory module 116 or at any other suitable location in system 100 such that the known signal may be accessed by processing system 112. If the generated signal for the particular detector 108 is the same as the known signal for the particular detector 108, processing system 112 may determine that an agent 102 is not present. If, however, the known signal for the particular detector 108 differs from the generated signal for the particular detector 108 (i.e., the generated signal constitutes an altered signal), processing system 112 may determine that an agent 102 is present (as the agent 102 absorbing a portion of the light emitted from the resonator 110 corresponding to the particular detector 108 may be the reason for the difference between the generated altered signal and the accessed signal).

Processing system 112 may be further operable to identify, in response to determining that an agent 102 is present, the agent 102 (or a family of the agent 102) based on the amount of light absorbed by the agent 102. For example, processing system 112 may determine an amount of light absorbed by the agent 102 by comparing the generated altered signal accessed from detectors 108 with the known signal associated with detectors 108. Having determined an amount of light absorbed by the agent 102 absorbed by each resonator 110, processing system 110 may access a plurality of agent profiles associated with a plurality of known agents 102 (e.g., from memory module 116 or any other suitable location in system 100), each profile indicating the light absorption characteristics of a particular known agent 102. For each resonator 110, processing system 112 may compare the determined amount of light absorbed by the agent 102 absorbed on the resonator 110 with the accessed agent profiles to determine the agent profile substantially matching the determined amount of light absorbed, thereby identifying the agent 102 absorbed on the surface of the resonator 110.

Furthermore, because different agents 102 may absorb different amounts of light at different peak wavelengths, the light absorption characteristics of the known agents 102 (as indicated in the agent profiles of the known agents 102) may account for the peak wavelengths at which absorption occurs. Additionally, because different resonators 110 of system 100 may be configured to transmit light at different peak wavelengths or ranges of peak wavelengths (as described above), the altered signals generated by detectors 108 and accessed by processing system 112 may be indicative of the peak wavelengths at which absorption occurs in the agent 102 absorbed on the surfaces of the corresponding resonators 110. Thus, in identifying the agent 102 absorbed on the surfaces of resonators 110 by matching the agent 102 with an agent profile, processing system 112 may account for the wavelengths at which absorption occurs, thereby increasing the accuracy of the identification.

As an additional example, each of the one or more resonators 110 may each be functionalized to attract a different agent 102 or family of agents 12 (as described above). Thus, by determining those detectors 108 generating altered signals (i.e., those detectors 108 generating signals that differ from the known signal, indicating absorption of light) and determining which agent 102 or family of agents 102 that the resonators 110 corresponding to those detectors 108 are functionalized to attract, processing system 112 may determine the agent 102 (or the family of the agent 102) absorbed on the surface of resonators 110.

Additionally or alternatively, processing system 112 may be operable to determine if an agent 102 is present (i.e., absorbed on the surface of one or more resonators 110) by analyzing the signals accessed from detectors 108 to determine if one or more of the accessed signals indicate a change in peak wavelength of light received by the detectors 108 (in a substantially similar manner to that discussed above with regard to changes intensity). For example, processing system 112 may access signals generated by detectors 108 and compare the signals accessed from detectors 108 with known signals associated with the detectors 108. If processing system 112 determines that any of the signals accessed from detectors 108 differ from known signals associated with detectors 108 (due to a change in peak wavelength of light received by detectors 108 caused by agent 102 absorbed by corresponding resonators 110), processing system 112 may determine that an agent 102 is present.

However, because the bandpass associated with a detector 108 (i.e., the range of peak wavelengths of light detectable to the detector 108) may be broader than the shift in wavelength caused by an agent 102 absorbed by a corresponding resonator 110, the detector 106 may not be able to detect a shift in wavelength caused by the agent 102. In other words, the signal generated by the detector 108 may be the same regardless of the peak wavelength shift caused by the agent 102. As a result, detectors 108 may have a corresponding tunable filters 118, which may permit the detectors 108 to detect minute shift in wavelength that may be otherwise undetectable (as described in further detail below with regard to FIGS. 3A-3B and FIGS. 4A-4C).

Although a particular implementation of system 100 is illustrated and primarily described, the present invention contemplates any suitable implementation of system 100 according to particular needs. Furthermore, although a particular number of components of system 100 have been illustrated and primarily described above, the present invention contemplates system 100 including any suitable number of such components.

In operation of an example embodiment of system 100 (limited for purposes of simplicity only to the context of a single resonator 110 configured to transmit light to a single detector 108 of detector array 106), resonator 110 receives an agent 102. Resonator 110 may transmit light received from a light source 104. Because the agent 102 may alter the intensity of the light transmitted by resonator 110 (as compared to the known intensity of light that would be transmitted by resonator 110 in the absence of the agent 102), the transmitted light may have an altered intensity. Assuming that the light transmitted by resonator 110 has an altered intensity caused by agent 102, detector 108 of detector array 106 receives the light having the altered intensity transmitted by resonator 110 and generates an altered signal corresponding to the transmitted light having the altered intensity. The generation of the altered signal (as opposed to the known signal) indicates the presence of agent 102, and agent 102 may be identified by processing system 112, as described below.

Processing system 112 accesses the altered signal generated by detector 108 of detector array 106 and determines an amount of light absorbed by the agent 102 by comparing the altered signal generated by detector 108 with a known signal. The known signal may be a signal corresponding to light having the known intensity (i.e., light transmitted by resonator 110 in the absence of agent 102). Based on the determined amount of light absorbed by agent 102, processing system 112 may compare the determined amount of light absorbed with absorption characteristics of a number of known agents 102 and identify the agent 102 received by resonator 110. For example, processing system 112 may identify the agent 102 received by resonator 110 as the agent 102 among the known agents 102 that has absorption characteristics most closely matching the determined amount of absorption.

Figure 2:
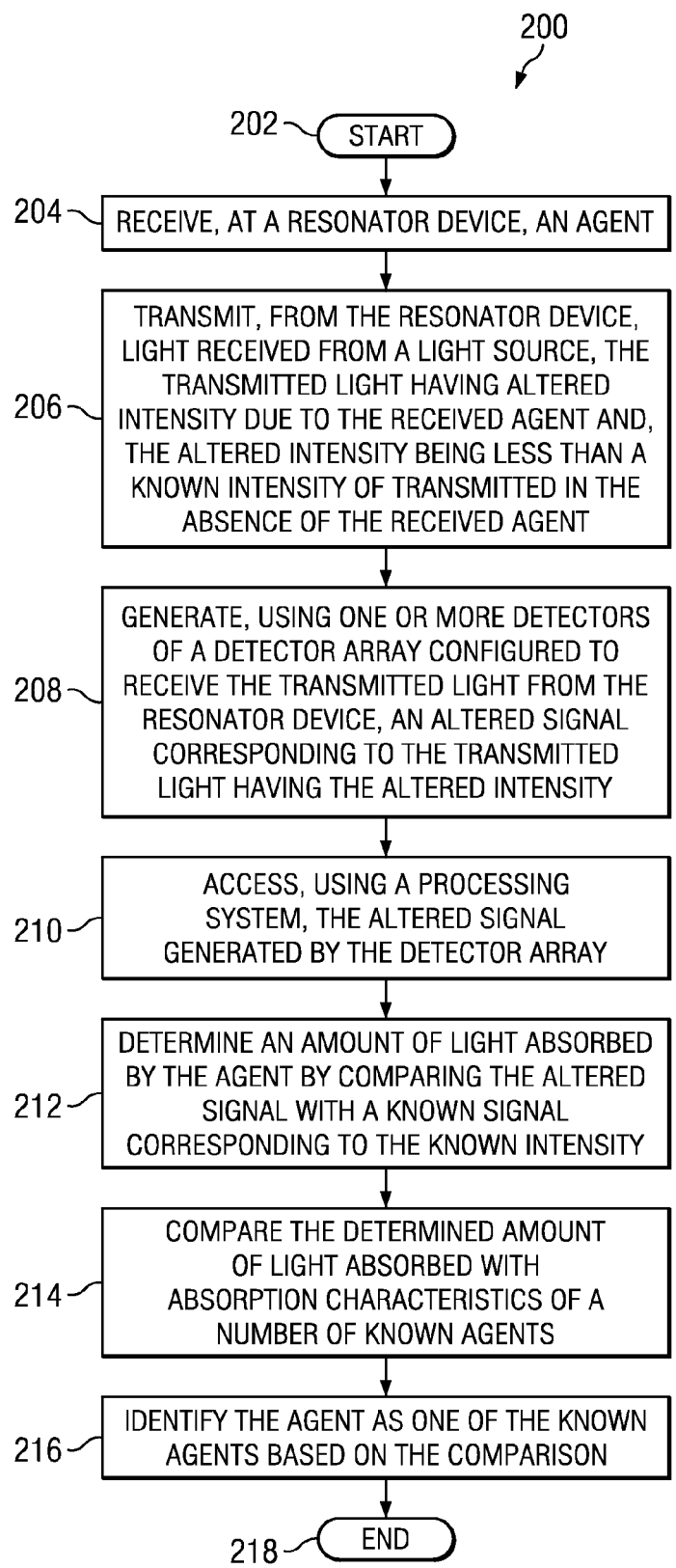
FIG. 2 illustrates an example method for detecting an agent, according to certain embodiments of the present invention.

FIG. 2 illustrates an example method 200 for detecting an agent 102, according to certain embodiments of the present invention. Although for purposes of simplicity the example method 200 is described in the context of a single resonator 110 configured to transmit light to a single detector 108 of detector array 106, the present invention contemplates any suitable number of resonators 110 each being configured to communicate with any suitable number of detectors 108 of a detector array 106.

The method begins at step 202. At step 204, resonator 110 receives an agent 102. Resonator 110 may be configured to receive an agent 102 by absorbing the agent 102 from a liquid including the agent 102, which may be deposited on a surface of resonator 110 (e.g., by a user). Alternatively, resonator 110 may be configured to receive an agent 102 (e.g., an airborne agent) by absorbing the agent 102 from air containing the agent 102. Furthermore, resonator 110 may be functionalized (e.g., by coating a surface of resonator 110 with artificial antibodies using a polymer technique) such that resonator 110 attracts only certain agents 102 or families of agents 102.

At step 206, resonator 110 transmits light received from a light source 104. Because the agent 102 may alter the intensity of the light transmitted by resonator 110 (as compared to the known intensity of light that would be transmitted by resonator 110 in the absence of the agent 102), the transmitted light may have an altered intensity. At step 208 (assuming that the light transmitted by resonator 110 has an altered intensity caused by agent 102), detector 108 of detector array 106 receives the light having the altered intensity transmitted by resonator 110 and generates an altered signal corresponding to the transmitted light having the altered intensity. The generation of the altered signal (as opposed to the known signal) indicates the presence of agent 102, and agent 102 may be identified by processing system 112, as described below.

At step 210, processing system 112 accesses the altered signal generated by detector 108 of detector array 106. At step 212, processing system determines an amount of light absorbed by the agent 102 by comparing the altered signal generated by detector 108 with a known signal. The known signal may be a signal corresponding to light having the known intensity (i.e., light transmitted by resonator 110 in the absence of agent 102). The known signal associated with the detector 108 may be stored in memory module 116 or at any other suitable location within system 100.

At step 214, processing system 112 compares the determined amount of light absorbed (caused by the agent 102) with absorption characteristics of a number of known agents 102. The absorption characteristics of the number of known agents 102 may be part of agent profiles for the number of known agents 102, the agent profiles being stored in memory module 116 or at any other suitable location in system 100 such that they may be accessed by processing system 112.

At step 216, processing system 112 identifies the agent 102 received by resonator 110 as the agent 102 among the known agents 102 having absorption characteristics most closely matching the determined amount of absorption. The method ends at step 218.

Figure 3A:
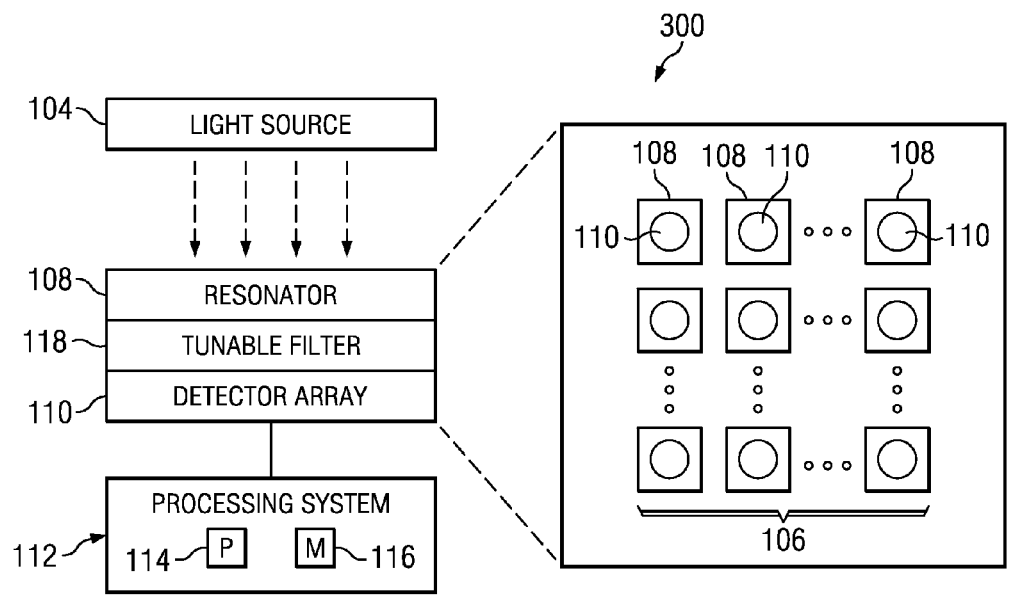
FIGS. 3A-3B illustrate an example alternative system for detecting an agent, according to certain embodiments of the present invention.
Figure 3B:
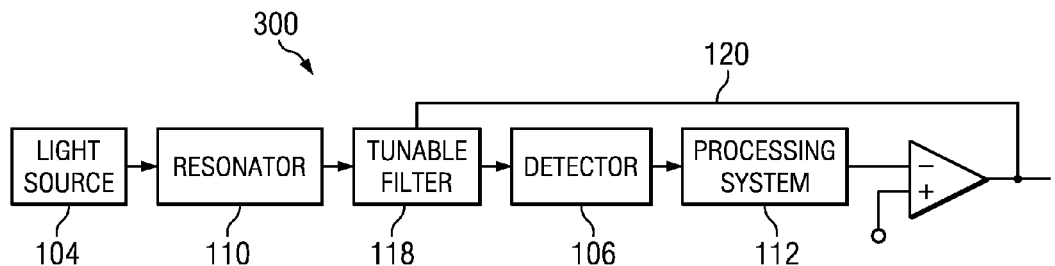

FIGS. 3A-3B illustrate an example alternative system 300 for detecting an agent 102, according to certain embodiments of the present invention. System 300 may include one or more light sources 104, a detector array 106 comprising one or more detectors 108, one or more resonators 110 configured to receive (e.g., absorb) an agent 102, and a processing system 112 (each of which is described above with regard to system 100 illustrated in FIG. 1). Moreover, each of these components of system 300 may be configured and operate in a substantially similar manner as described above with regard to FIG. 1.

In addition to the components of system 100 described above with regard to FIG. 1, system 300 may further include one or more tunable filters 118 each positioned between corresponding resonators 110 and detectors 108 of detector array 106 (i.e., each tunable filter 118 may correspond to a resonator 110 and a detector 108 of detector array 106). Because the bandpass associated with a detector 108 (i.e., the range of wavelengths of light for which the detector 108 is operable to generate a signal) may be broader than the shift in wavelength caused by an agent 102 absorbed on the surface of a resonator 110 (as described above), the detector 106 may not be able to detect the shift in wavelength caused by the agent 102. In other words, the signal generated by the detector 108 may be the same regardless of the peak wavelength shift caused by the agent 102. Accordingly, tunable filters 118 may facilitate the determination of an amount of the shift in wavelength caused by an agent 102 absorbed on the surface of a resonator 110, which may allow processing system 112 to determine the presence of and/or identify the agent 102, as described in further detail below.

Each tunable filters 118 may be operable to receive transmitted light from a corresponding resonator 110 and filter the transmitted light having peak wavelengths outside a range of peak wavelengths associated with (i.e., allowed to pass through) the tunable filter 118. The range of peak wavelengths associated with a tunable filter 118 (i.e., the bandpass of the tunable filter 118) may be narrower than the bandpass of the corresponding detector 108 such that transmitted light having wavelengths detectable by the detector 108 may be filtered by the tunable filter 118.

Furthermore, the range of peak wavelengths associated with (i.e., allowed to pass through) each tunable filter 118 may be variable. For example, a particular tunable filters 118 may have an associated first range of peak wavelengths such that the tunable filter 118 filters transmitted light received from the corresponding resonator 110 having wavelength outside the first range. Additionally, the particular tunable filter 118 may be operable to receive a signal. For example, the signal may be a voltage applied via a feedback control loop 120 controlled by processing system 112, as illustrated in FIG. 3B and described below. The received signal may cause the particular tunable filter 118 to filter transmitted light received from the corresponding resonator 110 having a wavelength outside a second range. In other words, the range of wavelengths outside which a tunable filter 118 filters transmitted light received from the corresponding resonator 110 may be dependent on an amount of signal (e.g., voltage) applied to the tunable filter 118.

Tunable filters 118 may be used (e.g., by processing system 112) in determining whether an agent 102 is present. As discussed above, each detector 108 of detector array 106 may be operable to generate a signal in response to light incident upon the detector 108 (i.e., light transmitted by the resonator 110 corresponding to the detector 108). However, because tunable filters 118 filter light transmitted by corresponding resonators 110, the corresponding detectors 108 may only generate a signal corresponding to light having a wavelength within the range of peak wavelengths associated with the corresponding tunable filter 118. In other words, transmitted light having peak wavelengths outside the range of peak wavelengths associated with the tunable filter 118 may not be received by the detector 106). Because an agent 102 absorbed on the surface of a resonator 110 may alter the peak wavelength at which the resonator 110 transmits light, the presence or absence of a signal generated by a detector 108 may be indicative of whether an agent 102 is present.

For example, a particular resonator 110 may have optical properties that cause the resonator 110 to transmit light having a known peak wavelength (in the absence of the agent 102) that falls within the range of peak wavelengths associated with the corresponding tunable filter 118. As a result, in the absence of an agent 102, a known signal will be generated by the corresponding detector 108 of detector array 106. However, an agent 102 absorbed on the surface of a resonator 110 may cause the light transmitted by the resonator 110 to have an altered peak wavelength that falls outside the range of peak wavelengths associated with the corresponding tunable filter 118. As a result, in the presence of the agent 102, a signal will not be generated by the corresponding detector 108 of detector array 106 (i.e., the transmitted light having the altered peak wavelength will not reach the detector 108 because the tunable filter 118 "blocks" the transmitted light).

Thus, if processing system 112 accesses the signals generated by the detectors 108 of detector array 106 (as described above) and determines that one or more of accessed signals differ from the known signals corresponding to those detectors 106 (because the one or more detectors 108 are not generating a signal since tunable filters 118 corresponding to the one or more detectors 108 are filtering the light transmitted by the corresponding resonators 110), processing system 112 may determine that an agent 102 has been absorbed on the surface of the one or more resonators 110.

Furthermore, if an agent 102 is determined to be present (e.g., based on the lack of a signal being generated by one or more detectors 108, as described above), tunable filters 118 may be used (e.g., by processing system 112) in identifying the agent 102. More particularly, tunable filters 118 may facilitate determining an amount of wavelength shift caused by an agent 102 absorbed on the surface of a resonator 110, and the amount of wavelength shift may be compared by processing system 112 with a number of known wavelength shifts associated with a number of known agents 102 to determine a match (i.e., the known wavelength shift having a value closest to the determined amount of wavelength shift). Based on the match, processing system 112 may identify the agent 102 absorbed on the surface of the resonator 110.

For example, as described above, the range of peak wavelengths associated with the tunable filters 118 may be variable based on an amount of voltage applied to the tunable filter 118. In other words, the amount of shift in the range of peak wavelengths associated with the tunable filters 118 may correspond to an amount of voltage applied to the tunable filter 118. Furthermore, processing system 112 (or any other suitable component of system 300) may be operable to maximize the signal being generated by detectors 108 of detector array 106 (i.e., maximize the intensity of light received by detectors 108) by controlling the amount of voltage applied to tunable filters 118 via a feedback control loop 120. Thus, based on the amount of voltage required to maximize the signal generated by a detector 108, processing system 112 may determine the wavelength shift in light transmitted by the corresponding resonator 110 between the known peak wavelength (i.e., when no agent 102 is absorbed on the corresponding resonator 110) and the altered peak wavelength (i.e., when no agent 102 is absorbed on the corresponding resonator 110).

Figure 4A:
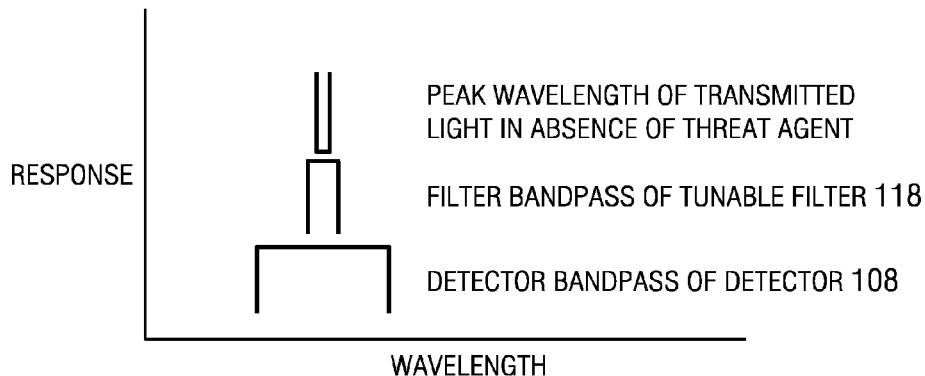
FIGS. 4A-4C illustrate example plots of response versus wavelength illustrating the operation of a tunable filter of the alternative system for detecting an agent illustrated in FIG. 3A-3B, according to certain embodiments of the present invention.
Figure 4B:
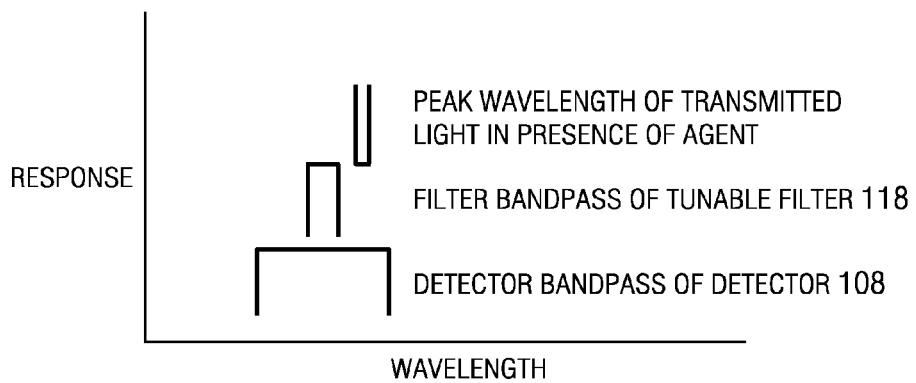
Figure 4C:
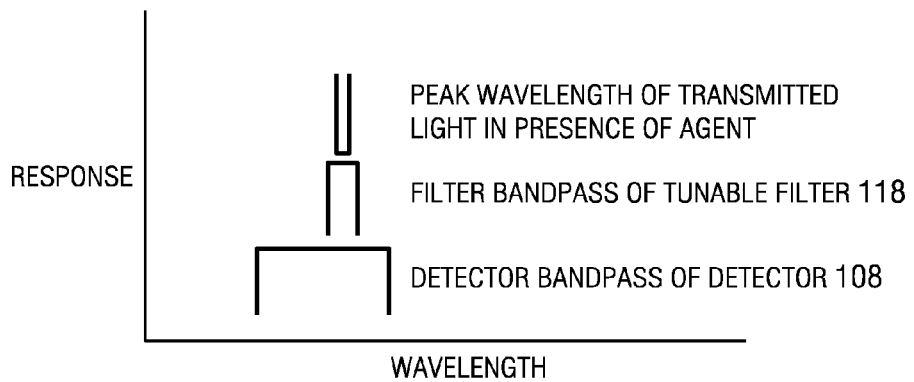

FIGS. 4A-4C illustrate example plots of response versus wavelength illustrating the operation of tunable filter 118 of system 300 (described above), according to certain embodiments of the present invention. FIG. 4A illustrates an example state of system 300 in which light is transmitted by a resonator 110 in the absence of an agent 102, the light having a known peak wavelength based on the optical properties of resonator 110. Furthermore, the known peak wavelength falls within the range of peak wavelengths associated with the corresponding tunable filter 118. Consequently, transmitted light having the known peak wavelength is not filtered by tunable filter 118 and reaches the corresponding detector 108 of detector array 106. Because the known peak wavelength falls within the range of wavelengths detectable by the corresponding detector 106 (i.e., within the bandpass of the corresponding detector 108), the corresponding detector 108 generates a signal (i.e., the known signal) corresponding to the received light.

FIG. 4B illustrates an example state of system 300 in which light is transmitted by a resonator 110 in the presence of an agent 102, the agent 102 changing the index of refraction of light received by resonator 110 such that the transmitted light has an altered peak wavelength. Furthermore, the altered peak wavelength falls outside the range of peak wavelengths associated with the corresponding tunable filter 118. Consequently, the transmitted light having the altered peak wavelength is filtered by tunable filter 118 and does not reach the corresponding detector 108 of detector array 106. Because the transmitted light does not reach the corresponding detector 106, the corresponding detector 106 does not generate a signal (which, as discussed above, indicates the presence of the agent 102).

FIG. 4C illustrates an example state of system 300 similar to that described above with regard to FIG. 4B except that in FIG. 4C a voltage has been applied to the corresponding tunable filter 118 via a feedback control loop 120, the applied voltage altering the range of peak wavelengths associated with the corresponding tunable filter 118 such that the altered peak wavelength of the transmitted light falls within the altered range of peak wavelengths associated with the corresponding tunable filter 118. Consequently, the transmitted light having the altered peak wavelength is not filtered by tunable filter 118 and reaches the corresponding detector 108 of detector array 106. Because the altered peak wavelength falls within the range of wavelengths detectable by the corresponding detector 106 (i.e., is within the bandpass of the corresponding detector 108), the corresponding detector 108 generates a signal (i.e., the altered signal) corresponding to the received light. Moreover, because the amount of shift in the range of peak wavelengths of the corresponding tunable filter 118 corresponds to the amount of applied voltage, the amount of shift in wavelength caused by the agent 102 may be determined.

Returning to FIG. 3, assuming that an agent 102 is absorbed on the surface of resonators 110, processing system 112 may access the voltage applied via feedback control loops 120 to each tunable filter 118 that maximizes the signal generated by the corresponding detectors 108 (the voltage applied being known to processing system due to the fact that the voltage is applied via feedback control loop 120). Based on the applied voltages, processing system 112 may determine the amount of wavelength shift in light transmitted by each resonator 110 caused by the agent 102 absorbed on each resonator 110. Processing system 112 may then compare the determined wavelength shifts with accessed known wavelength associated with a plurality of known agents 102 (e.g., from memory module 116) to determine a match for each resonator 110 (i.e., the known wavelength shift having a value closest to the determined amount of wavelength shift in light transmitted by each resonator 110). Based on the match, processing system 112 may identify the agent 102 absorbed on the surface of the resonator 110.

Furthermore, because different agents 102 may shift peak wavelengths to a greater degree at or near particular wavelengths, the known wavelengths shifts associated with the plurality of known agents profiles of agents 102 may take into account the wavelengths at which the peak wavelength shift occurs. Additionally, because different resonators 110 of system 100 may be configured to transmit light at different peak wavelengths or ranges of peak wavelengths (as described above), the voltages applied to the different tunable filters 118 accessed by processing system 112 may be indicative of an amount of wavelength shift associated with light having particular peak wavelengths (i.e., the known peak wavelengths of light transmitted by the resonators 110). Thus, in identifying the agent 102 absorbed on the surface of resonators 110 by matching the agent 102 with an agent profile, processing system 112 may account for the wavelengths at which different wavelength shifts occur, thereby increasing the accuracy of the identification.

In addition to determining the shift in peak wavelength of the transmitted light caused by an agent 102, processing system 112 may be further operable to determine an amount of light absorbed by the agent 102. For example, if an agent 102 is absorbed on the surface of a resonator 110 (causing a shift in peak wavelength of light transmitted by the resonator 110) and a voltage has been applied to the corresponding tunable filter 118 such that the transmitted light is received by the corresponding detector 108, it may be possible to determine an amount of light absorbed by the agent 102 based on the altered signal generated by the detector 108 in a manner substantially similar to that described above with regard to FIG. 1. Accordingly, processing system 112 may compare a determined shift in peak wavelength of transmitted light and the determined amount of transmitted light absorbed with corresponding components of a plurality of agent profiles to identify the agent 102. Because the identification is based on multiple characteristics of light (i.e., peak wavelength shift and absorption), the accuracy of the identification may be further increased.

In operation of an example embodiment of system 300 (limited for purposes of simplicity only to the context of a single resonator 110 configured to transmit light to a single detector 108 of detector array 106) resonator 110 receives an agent 102. Resonator 110 may transmit light received from a light source 104. The agent 102 may alter the index of refraction of resonator 110 such that the light transmitted by resonator 110 may have an altered peak wavelength (as compared to the known peak wavelength of light that would be transmitted by resonator 110 in the absence of the agent 102).

Assuming that the light transmitted by resonator 110 has an altered peak wavelength caused by agent 102, tunable filter 118 filters the transmitted light having the altered peak wavelength such that the transmitted light having the altered peak wavelength does not reach detector 108 of a detector array 106 (due to the fact that tunable filter 118 is configured to filter the portion of the transmitted light received from resonator 110 having a peak wavelength outside a first range of peak wavelengths, the altered peak wavelength being outside the first range). Processing system 112 determines that detector 108 of detector array 106 is not generating a signal (because the transmitted light is filtered by tunable filter 118), the absence of the signal being generated by detector 108 indicating the presence of the agent 102.

In response to a determination that an agent 102 is present, an amount of signal (e.g., voltage) may be applied to tunable filter 118. The amount of signal may cause tunable filter 118 to filter transmitted light having a peak wavelength outside a second range of peak wavelengths, the altered peak wavelength being within the second range of peak wavelengths. Thus, the transmitted light having the altered peak wavelength may be received by detector 108 of detector array 106.

Detector 108 of detector array 106 receives the transmitted light having the altered peak wavelength and generates a signal corresponding to the received transmitted light having the altered peak wavelength. In response to a determination that detector 108 is generating a signal (or that the signal generated by detector 108 has been maximized), processing system 112 accesses the amount of signal applied to the tunable filter 118 and determines, based on the accessed amount of signal applied to tunable filter 118, a wavelength shift corresponding to the difference between the known peak wavelength and the altered peak wavelength. Processing system 112 compares the determined wavelength shift with a number of wavelength shifts corresponding to a number of known agents 102 and identifies the agent 102 as the agent 102 among the known agents 102 having a wavelength shift most closely matching the determined wavelength shift.

FIG. 5 illustrate an example alternative method 500 for detecting an agent 102, according to certain embodiments of the present invention. Although for purposes of simplicity the example alternative method 500 is described in the context of a single resonator 110 configured to transmit light to a single detector 108 of detector array 106, the present invention contemplates any suitable number of resonators 110 each being configured to communicate with any suitable number of detectors 108 of a detector array 106.

The method begins at step 502. At step 504, resonator 110 receives an agent 102. Resonator 110 may be configured to receive an agent 102 by absorbing the agent 102 from a liquid including the agent 102, which may be deposited on a surface of resonator 110 (e.g., by a user). Alternatively, resonator 110 may be configured to receive an agent 102 (e.g., an airborne agent) by absorbing the agent 102 from air containing the agent 102. Furthermore, resonator 110 may be functionalized (e.g., by coating a surface of resonator 110 with artificial antibodies using a polymer technique) such that resonator 110 attracts only certain agents 102 or families of agents 102.

At step 506, resonator 110 transmits light received from a light source 104. The agent 102 may alter the index of refraction of resonator 110 such that the light transmitted by resonator 110 may have an altered peak wavelength (as compared to the known peak wavelength of light that would be transmitted by resonator 110 in the absence of the agent 102).

At step 508 (assuming that the light transmitted by resonator 110 has an altered peak wavelength caused by agent 102), tunable filter 118 filters the transmitted light having the altered peak wavelength such that the transmitted light having the altered peak wavelength does not reach detectors 108 of a detector array 106 (which are configured to receive transmitted light not filtered by tunable filter 118). As described above, tunable filter 118 may be configured to receive the transmitted light from the resonator 110 and filter the portion of the transmitted light having a peak wavelength outside a first range of peak wavelengths. Because the known peak wavelength is within the first range and the altered peak wavelength is outside the first range, the tunable filter 118 filter all light having the altered peak wavelength, thereby prohibiting the transmitted light from reaching detector 108.

At step 510, processing system 112 determines that detector 108 of detector array 106 is not generating a signal. Because the known peak wavelength (i.e., the peak wavelength of light transmitted by resonator 110 in the absence of agent 102) is within the first range of peak wavelengths of tunable filter 118 and the altered peak wavelength (i.e., the peak wavelength of light transmitted by resonator 110 in the presence of agent 102) is outside the first range of peak wavelengths of tunable filter 118, the absence of the signal being generated by detector 108 of detector array 106 indicates the presence of the agent 102.

In response to a determination that an agent 102 is present, an amount of signal (e.g., voltage) may be applied to tunable filter 118 at step 512. In certain embodiments, processing system 112 may apply the amount of voltage to tunable filter 118 via feedback control loop 120. The received amount of signal may cause tunable filter 118 to filter the transmitted light having a peak wavelength outside a second range of peak wavelengths as opposed to the first range of peak wavelengths. Moreover, the altered peak wavelength may be within the second range of peak wavelengths such that the light transmitted by resonator 110 having the altered peak wavelength may be received by detector 108 of detector array 106.

At step 514, detector 108 of detector array 106 receives the transmitted light having the altered peak wavelength and, at step 516, detector 108 generates a signal corresponding to the received transmitted light having the altered peak wavelength. In response to a determination that detector 108 is generating a signal (or that the signal generated by detector 108 has been maximized), processing system 112 accesses the amount of signal applied to the tunable filter 118 at step 518. At step 520, processing system determines, based on the accessed amount of signal applied to tunable filter 118, a wavelength shift corresponding to the difference between the known peak wavelength and the altered peak wavelength.

At step 522, processing system compares the determined wavelength shift with a number of known wavelength shifts of agent profiles corresponding to a number of known agents 102, the agent profiles being accessed by processing system 112 from memory module 116 or any other suitable location within system 100. At step 524, processing system 112 identifies the agent 102 as the agent 102 among the known agents 102 having a known wavelength shift most closely matching the determined wavelength shift. The method ends at step 526.

Particular embodiments of the present invention may provide one or more technical advantages. For example, embodiments of the present invention may use a detector array 106 (such as an FPA) to detect changes in characteristics of light passing through an agent 102. As a result, embodiments of the present invention may be incorporated into a portable device, which may reduce size, weight, cost, and power requirements as compared to certain convention systems for detecting an agent 102. Moreover, because embodiments of the present invention may use detector arrays 106 which may be common in certain imaging devices, the present invention may be integrated with or form part of an imaging device.

Although the present invention has been described with several embodiments, diverse changes, substitutions, variations, alterations, and modifications may be suggested to one skilled in the art, and it is intended that the invention encompass all such changes, substitutions, variations, alterations, and modifications as fall within the spirit and scope of the appended claims.

What is claimed is:
1. An agent detection system, comprising:
   a resonator device configured to:
      receive an agent;

transmit light received from a light source, the transmitted light having an altered peak wavelength due to the presence of the received agent, the altered peak wavelength being different than a known peak wavelength of light transmitted by the resonator device in the absence of the received agent;

a filter device configured to filter the transmitted light having the altered peak wavelength such that the transmitted light having the altered peak wavelength does not reach one or more detectors of a detector array configured to receive transmitted light not filtered by the filter device, the filter device configured to receive the transmitted light from the resonator device and filter the transmitted light having a peak wavelength outside a first range of peak wavelengths, the known peak wavelength being within the first range and the altered peak wavelength being outside the first range; and a processing system operable to determine that the one or more detectors of the detector array are not generating a signal, the absence of the signal being generated by the one or more detectors of the detector array indicating the presence of the agent.

2. The system of claim 1, wherein the detector array comprises a focal plane array (FPA).

3. The system of claim 1, wherein:

the filter device is operable to receive an amount of signal in response to the determination that the one or more detectors of the detector array are not generating a signal, the received amount of signal causing the filter device to filter the transmitted light having a peak wavelength outside a second range of peak wavelengths, the altered peak wavelength being within the second range of peak wavelengths; and the system further comprises the detector array comprising the one or more detectors, the one or more detectors operable to:

receive the transmitted light having the altered peak wavelength; and generate a signal corresponding to the received transmitted light having the altered peak wavelength.

4. The system of claim 3, wherein the processing system is further operable to:

access the amount of signal applied to the filter device;

determine, based on the amount of signal applied to the filter device, a wavelength shift corresponding to the difference between the known peak wavelength and the altered peak wavelength;

compare the determined wavelength shift with a number of wavelength shifts corresponding to a number of known agents; and identify the agent based on the comparison.

5. The system of claim 3, wherein:

the light transmitted by the resonator device has an altered intensity due to the presence of the received agent, the altered intensity being less than a known intensity of light transmitted by the resonator device in the absence of the received agent;

the one or more detectors of the detector array are further operable to generate an altered signal corresponding to light having the altered intensity;

the processing system is further operable to:

access the amount of signal applied to the filter device;

determine, based on the amount of signal applied to the filter device, a wavelength shift corresponding to the difference between the known peak wavelength and the altered peak wavelength;

access the altered signal generated by the detector array;

determine an amount of light absorbed by the agent by comparing the altered signal with a known signal corresponding to the known intensity;

compare the determined wavelength shift with wavelength shifts corresponding to a number of known agents and compare the determined amount of light absorbed with absorption characteristics of a number of known agents; and identify the threat agent based on the comparisons.

6. The system of claim 4, wherein the processing system comprises a read-out integrated circuit (ROIC) coupled to the detector array.

7. The system of claim 1, wherein the resonator device comprises chalcogenide glass.

8. The system of claim 1, wherein the resonator device comprises an optical cavity.

9. The system of claim 1, wherein the light source comprises an on-chip quantum dot light-emitting diode (LED).

10. The system of claim 1, wherein the light source comprises an on-chip laser.

11. A method for detecting an agent, comprising:

receiving, at a resonator device, an agent;

transmitting, from the resonator device, light received from a light source, the transmitted light having an altered peak wavelength due to the presence of the received agent, the altered peak wavelength being different than a known peak wavelength of light transmitted by the resonator device in the absence of the received agent;

filtering the transmitted light having the altered peak wavelength at a filter device such that the transmitted light having the altered peak wavelength does not reach one or more detectors of a detector array configured to receive transmitted light not filtered by the filter device, the filter device configured to receive the transmitted light from the resonator device and filter the transmitted light having a peak wavelength outside a first range of peak wavelengths, the known peak wavelength being within the first range and the altered peak wavelength being outside the first range; and determining, using a processing system, that the one or more detectors of the detector array are not generating a signal, the absence of the signal being generated by the one or more detectors of the detector array indicating the presence of the agent.

12. The method of claim 11, wherein the detector array comprises a focal plane array (FPA).

13. The method of claim 11, further comprising:

receiving, at the filter device, an amount of signal in response to the determination that the one or more detectors of the detector array are not generating a signal, the received amount of signal causing the filter device to filter the transmitted light having a peak wavelength outside a second range of peak wavelengths, the altered peak wavelength being within the second range of peak wavelengths;

receiving, at the detector array, the transmitted light having the altered peak wavelength; and generating, using the one or more detectors of the detector array, a signal corresponding to the received transmitted light having the altered peak wavelength.

14. The method of claim 13, further comprising:

accessing, using a processing system, the amount of signal applied to the filter device;

determining, based on the amount of signal applied to the filter device, a wavelength shift corresponding to the difference between the known peak wavelength and the altered peak wavelength;

comparing the determined wavelength shift with a number of wavelength shifts corresponding to a number of known agents; and identifying the agent based on the comparison.

15. The method of claim 13, wherein:

the light transmitted by the resonator device has an altered intensity due to the presence of the received agent, the altered intensity being less than a known intensity of light transmitted by the resonator device in the absence of the received agent;

the method further comprising:

generating, using one or more detectors of the detector array, an altered signal corresponding to the transmitted light having the altered intensity;

accessing, using a processing system, the amount of signal applied to the filter device;

determining, based on the amount of signal applied to the filter device, a wavelength shift corresponding to the difference between the known peak wavelength and the altered peak wavelength;

accessing, using the processing system, the altered signal generated by the detector array;

determining an amount of light absorbed by the agent by comparing the altered signal with a known signal corresponding to the known intensity comparing the determined wavelength shift with wavelength shifts corresponding to a number of known agents and comparing the determined amount of light absorbed with absorption characteristics of a number of known agents; and identifying the threat agent based on the comparisons.

16. The method of claim 14, wherein the processing system comprises a read-out integrated circuit (ROIC) coupled to the detector array.

17. The method of claim 11, wherein the resonator device comprises chalcogenide glass.

18. The method of claim 11, wherein the resonator device comprises an optical cavity.

19. The method of claim 11, wherein the light source comprises an on-chip quantum dot light-emitting diode (LED).

20. The method of claim 11, wherein the light source comprises an on-chip laser.

21. An agent detection system, comprising:

a resonator device configured to:

receive an agent;

transmit light received from a light source, the transmitted light having an altered peak wavelength due to the presence of the received agent;

a filter device configured to filter the transmitted light, the filter device operable to receive an amount of signal that causes the filter device to filter the transmitted light having a peak wavelength outside a second range of peak wavelengths rather than wavelengths outside a first range of peak wavelengths, the altered peak wavelength being within the second range of peak wavelengths but outside the first range of peak wavelengths; and a focal plane array comprising the one or more detectors, the one or more detectors operable to:

receive the transmitted light having the altered peak wavelength; and generate a signal corresponding to the received transmitted light having the altered peak wavelength;

a processing system operable to:

access the amount of signal applied to the filter device;

determine, based on the amount of signal applied to the filter device, a wavelength shift corresponding to the difference between the altered peak wavelength and a known peak wavelength, the known peak wavelength being the peak wavelength of light transmitted by the resonator device in the absence of the received agent;

compare the determined wavelength shift with a number of wavelength shifts corresponding to a number of known agents; and identify the agent based on the comparison.

* * * * *